United States Patent
Kim et al.

(10) Patent No.: US 12,257,341 B2
(45) Date of Patent: *Mar. 25, 2025

(54) INJECTABLE COMPOSITION CONTAINING PRODRUG OF CASPASE INHIBITORS, AND PREPARATION METHOD THEREFOR

(71) Applicant: LG CHEM, LTD., Seoul (KR)

(72) Inventors: Sung Won Kim, Seoul (KR); Jae Uk Baek, Seoul (KR); Hyun Seo Park, Seoul (KR); Myung Won Jin, Seoul (KR); Jung Gyu Park, Seoul (KR); Bok Tae Kim, Seoul (KR); Sei Hyun Choi, Seoul (KR)

(73) Assignee: LG CHEM, LTD., Seoul (KR)

( * ) Notice: Subject to any disclaimer, the term of this patent is extended or adjusted under 35 U.S.C. 154(b) by 625 days.

This patent is subject to a terminal disclaimer.

(21) Appl. No.: 17/614,881

(22) PCT Filed: May 29, 2020

(86) PCT No.: PCT/KR2020/006953
§ 371 (c)(1),
(2) Date: Nov. 29, 2021

(87) PCT Pub. No.: WO2020/242234
PCT Pub. Date: Dec. 3, 2020

(65) Prior Publication Data
US 2022/0226234 A1    Jul. 21, 2022

(30) Foreign Application Priority Data
May 31, 2019 (KR) .................. 10-2019-0064304

(51) Int. Cl.
| A61K 9/00 | (2006.01) |
| A61K 9/16 | (2006.01) |
| A61K 9/19 | (2006.01) |
| A61K 31/4725 | (2006.01) |
| A61K 41/17 | (2020.01) |

(52) U.S. Cl.
CPC .............. *A61K 9/0019* (2013.01); *A61K 9/16* (2013.01); *A61K 9/1647* (2013.01); *A61K 9/1682* (2013.01); *A61K 9/19* (2013.01); *A61K 31/4725* (2013.01); *A61K 41/17* (2020.01)

(58) Field of Classification Search
CPC ...... A61K 9/0019; A61K 9/16; A61K 9/1647; A61K 9/1682; A61K 9/19; A61K 31/4725; A61K 41/17; A61K 9/0024; A61P 19/08; A61P 19/02; A61P 29/00
See application file for complete search history.

(56) References Cited

U.S. PATENT DOCUMENTS

| 2003/0216290 A1* | 11/2003 | Lecomte | ................ A61K 38/08 514/18.9 |
| 2006/0223848 A1* | 10/2006 | Chang | .................. C07D 413/12 514/378 |
| 2016/0022583 A1 | 1/2016 | Lee et al. | |

FOREIGN PATENT DOCUMENTS

| EP | 3395364 A1 | 10/2018 |
| KR | 10-2009-0116494 A | 11/2009 |
| KR | 10-2014-0120496 A | 10/2014 |
| WO | 2006-090997 A1 | 8/2006 |
| WO | 2010-005765 A1 | 1/2010 |

OTHER PUBLICATIONS

International Search Report dated Sep. 4, 2020, issued in the corresponding international application No. PCT/KR2020/006953, 6 pages.

* cited by examiner

*Primary Examiner* — Lezah Roberts
*Assistant Examiner* — Abdulrahman Abbas
(74) *Attorney, Agent, or Firm* — ROTHWELL, FIGG, ERNST & MANBECK, P.C.

(57) ABSTRACT

The present invention relates to an injectable pharmaceutical composition containing a prodrug of caspase inhibitors, and a preparation method therefor. More specifically, the present invention relates to an injectable pharmaceutical composition, and a preparation method therefor, the composition comprising, as an active ingredient, (2S,3S)-2-(fluoromethyl)-3-((R)-5-isopropyl-3-(isoquinolin-1-yl)-4,5-dihydroisoxazole-5-carboxamido)-5-oxotetrahydrofuran-2-yl acetate, which is a prodrug of caspase inhibitors, or a pharmaceutically acceptable salt or isomer thereof, and comprising, as a biocompatible polymer, microspheres containing poly(lactide-co-glycolide).

30 Claims, 8 Drawing Sheets

[Fig. 1]

(a) Example 1

(b) Example 2

(c) Example 3

(d) Example 4

(e) Example 5

(f) Example 6

[Fig. 1 – Cont.]

(g) Example 7

INJECTABLE COMPOSITION CONTAINING PRODRUG OF CASPASE INHIBITORS, AND PREPARATION METHOD THEREFOR

CROSS-REFERENCE TO RELATED APPLICATION(S)

This application is a 35 U.S.C. § 371 National Phase Entry Application from PCT/KR2020/006953, filed on May 29, 2020 and designating the United States, which claims the benefit of priority from Korean Patent Application No. 10-2019-0064304, filed on May 31, 2019 with the Korean Intellectual Property Office, all of the full disclosures of which are incorporated herein by reference.

TECHNICAL FIELD

The present invention relates to a pharmaceutical composition for injection comprising a caspase inhibitor prodrug and a method of preparation therefor. More specifically, the present invention relates to a pharmaceutical composition for injection comprising a microsphere which comprises (2S,3S)-2-(fluoromethyl)-3-((R)-5-isopropyl-3-(isoquinolin-1-yl)-4,5-dihydroisoxazole-5-carboxamido)-5-oxotetrahydrofuran-2-yl acetate, or a pharmaceutically acceptable salt or isomer thereof as an active ingredient; and poly(lactide-co-glycolide) as a biocompatible polymer, and a method of preparation therefor.

BACKGROUND ART

Caspases are a type of enzymes and are cysteine proteases that exist as an α2β2 tetramer. Caspase inhibitors interfere with the activity of these caspases, thereby regulating inflammation or apoptosis caused by the action of caspases. Diseases in which symptoms can be eliminated or alleviated by administration of these compounds include osteoarthritis, rheumatoid arthritis, degenerative arthritis, destructive bone disorder, hepatic diseases caused by hepatitis virus, acute hepatitis, hepatocirrhosis, brain damage caused by hepatitis virus, human fulminant liver failure, sepsis, organ transplantation rejection, ischemic cardiac disease, dementia, stroke, brain impairment due to AIDS, diabetes, gastric ulcer, etc.

Among compounds having various structures known as caspase inhibitors, isoxazoline derivatives were filed as Korean Patent Application Nos. 10-2004-0066726, 10-2006-0013107 and 10-2008-0025123. In addition, a prodrug of a caspase inhibitor based on an isoxazoline derivative was disclosed in International Publication No. WO 2007/015931 (Applicant: Vertex Pharmaceuticals Incorporated, USA).

Meanwhile, nivocasan ((R)—N-((2S,3S)-2-(fluoromethyl)-2-hydroxy-5-oxotetrahydrofuran-3-yl]-5-isopropyl-3-(isoquinolin-1-yl)-4,5-dihydroisoxazole-5-carboxamide) of the following Formula 2 is attracting attention as an effective caspase inhibitor.

[Formula 2]

However, when nivocasan is prepared as a polymeric microsphere formulation in a sustained-release formulation, a large amount of drug is lost during the preparation process according to its physicochemical properties, resulting in low encapsulation efficiency, and there is a limit to the in vitro drug release period.

DISCLOSURE OF INVENTION

Technical Problem

Accordingly, the technical problem of the present invention is the provision of a composition for injection in which there is no initial burst release and the release period of the drug is greatly increased when a sustained-release formulation of a caspase inhibitor is prepared.

In addition, another technical problem of the present invention is the provision of a method for efficiently preparing the composition for injection.

Solution to Problem

In order to solve the above technical problem, the present invention provides a pharmaceutical composition for injection comprising a microsphere which comprises (2S,3S)-2-(fluoromethyl)-3-((R)-5-isopropyl-3-(isoquinolin-1-yl)-4,5-dihydroisoxazole-5-carboxamido)-5-oxotetrahydrofuran-2-yl acetate of the following Formula 1, or a pharmaceutically acceptable salt or isomer thereof as an active ingredient; and poly(lactide-co-glycolide) as a biocompatible polymer:

[Formula 1]

In addition, to solve another technical problem, the present invention provides a method for preparing a pharmaceutical composition for injection comprising: i) preparing a dispersed phase by dissolving (2S,3 S)-2-(fluoromethyl)-3-((R)-5-isopropyl-3-(isoquinolin-1-yl)-4,5-dihydroisoxazole-5-carboxamido)-5-oxotetrahydrofuran-2-yl acetate, or a pharmaceutically acceptable salt or isomer thereof as an active ingredient; and poly(lactide-co-glycolide) as a biocompatible polymer in an organic solvent; ii) preparing an emulsion by adding the dispersed phase obtained in step (i) to a continuous phase; and iii) removing a solvent from the emulsion obtained in step (ii) and freeze-drying to obtain a microsphere.

The present invention is described in detail hereinafter.

According to one aspect of the present invention, there is provided a pharmaceutical composition for injection comprising a microsphere which comprises (2S,3S)-2-(fluoromethyl)-3-((R)-5-isopropyl-3-(isoquinolin-1-yl)-4,5-dihydroisoxazole-5-carboxamido)-5-oxotetrahydrofuran-2-yl acetate of Formula 1 (hereinafter referred to as "Compound of Formula 1"), or a pharmaceutically acceptable salt or isomer thereof as an active ingredient; and poly(lactide-co-glycolide) as a biocompatible polymer.

In the present invention, the Compound of Formula 1 may form a pharmaceutically acceptable salt. A pharmaceutically acceptable salt may include an acid-addition salt which is formed from an inorganic acid such as hydrochloric acid, sulfuric acid, nitric acid, phosphoric acid, hydrobromic acid and hydroiodic acid; an organic acid such as tartaric acid, formic acid, citric acid, acetic acid, trichloroacetic acid, trifluoroacetic acid, gluconic acid, benzoic acid, lactic acid, fumaric acid, maleic acid and salicylic acid; or sulfonic acid such as methanesulfonic acid, ethanesulfonic acid, benzenesulfonic acid and p-toluenesulfonic acid, which form non-toxic acid-addition salt including pharmaceutically acceptable anion. In addition, a pharmaceutically acceptable carboxylic acid salt includes the salt with alkali metal or alkali earth metal such as lithium, sodium, potassium, calcium and magnesium; salts with amino acid such as lysine, arginine and guanidine; an organic salt such as dicyclohexylamine, N-methyl-D-glucamine, tris(hydroxymethyl)methylamine, diethanolamine, choline and triethylamine. The compound of Formula 1 according to the present invention may be converted into their salts by conventional methods.

Meanwhile, since the Compound of Formula 1 according to the present invention can have an asymmetric carbon center and asymmetric axis or plane, they can exist as E- or Z-isomer, R- or S-isomer, racemic mixtures or diastereoisomer mixtures and each diastereoisomer, all of which are within the scope of the present invention.

Herein, unless indicated otherwise, the term "the Compound of Formula 1" is used to mean all the Compound of Formula 1, pharmaceutically acceptable salts and isomers thereof.

In one embodiment of the present invention, the weight ratio of the Compound of Formula 1, or a pharmaceutically acceptable salt or isomer thereof to poly(lactide-co-glycolide) (the weight of the Compound of Formula 1/the weight of poly(lactide-co-glycolide)) may be preferably 0.01 to 0.7, and more preferably 0.1 to 0.4. In one embodiment of the present invention, the weight ratio of the Compound of Formula 1, or a pharmaceutically acceptable salt or isomer thereof to poly(lactide-co-glycolide) may be 0.2.

In one embodiment of the present invention, the poly (lactide-co-glycolide)(PLGA) as a biocompatible polymer may be polymerized from lactide and glycolide by ring-opening polymerization in the presence of a catalyst. In one embodiment of the present invention, a molar ratio of lactide to glycolide of the poly(lactide-co-glycolide) may be preferably 40:60 to 90:10, and more preferably 70:30 to 90:10. In one embodiment of the present invention, the molar ratio of lactide to glycolide of the poly(lactide-co-glycolide) may be 85:15. In one embodiment of the present invention, the poly(lactide-co-glycolide) may be used in a mixture having different molar ratios of lactide to glycolide. For example, as the poly(lactide-co-glycolide), those having a molar ratio of lactide to glycolide of 50:50 and 75:25 may be mixed and used, or those having a molar ratio of lactide to glycolide of 75:25 and 85:15 may be mixed and used.

In one embodiment of the present invention, the molecular weight of the poly(lactide-co-glycolide) may be preferably 1 to 1,000 kDa, and more preferably 75 to 400 kDa.

In one embodiment of the present invention, the poly (lactide-co-glycolide) may have an ester or an acid, and more preferably an ester as an end group.

In one embodiment of the present invention, the pharmaceutical composition for injection may further comprise a solvent. Examples of the solvent include, but are not limited to, water, saline or phosphate-buffered saline.

The pharmaceutical composition for injection according to the present invention may further comprise other ingredients such as a dispersing agent, a wetting agent or a suspending agent, if necessary.

Exemplary diseases that can be prevented or treated by the pharmaceutical composition for injection according to the present invention include, but are not limited to, those selected from apoptosis-associated diseases, inflammatory diseases, osteoarthritis, rheumatoid arthritis, degenerative arthritis and destructive bone disorders.

In one embodiment of the present invention, the pharmaceutical composition for injection according to the present invention may be used for the prevention, treatment or pain relief of osteoarthritis.

According to another aspect of the present invention, there is provided a method for preparing a pharmaceutical composition for injection comprising: i) preparing a dispersed phase by dissolving the Compound of Formula 1, or a pharmaceutically acceptable salt or isomer thereof as an active ingredient; and poly(lactide-co-glycolide) as a biocompatible polymer in an organic solvent; ii) preparing an emulsion by adding the dispersed phase obtained in step (i) to a continuous phase; and iii) removing a solvent from the emulsion obtained in step (ii) and freeze-drying to obtain a microsphere.

In one embodiment of the present invention, the weight ratio of the Compound of Formula 1, or a pharmaceutically acceptable salt or isomer thereof to poly(lactide-co-glycolide) (the weight of the Compound of Formula 1/the weight of poly(lactide-co-glycolide)) in step (i) may be preferably 0.01 to 0.7, and more preferably 0.1 to 0.4. In one embodiment of the present invention, the weight ratio of the Compound of Formula 1, or a pharmaceutically acceptable salt or isomer thereof to poly(lactide-co-glycolide) may be 0.2.

In one embodiment of the present invention, the molar ratio of lactide to glycolide of the poly(lactide-co-glycolide) may be preferably 40:60 to 90:10, and more preferably 70:30 to 90:10. In one embodiment of the present invention, the molar ratio of lactide to glycolide of the poly(lactide-co-glycolide) may be 85:15. In one embodiment of the present invention, the poly(lactide-co-glycolide) may be used in a mixture having different molar ratios of lactide to glycolide. For example, as the poly(lactide-co-glycolide), those having a molar ratio of lactide to glycolide of 50:50 and 75:25 may be mixed and used, or those having a molar ratio of lactide to glycolide of 75:25 and 85:15 may be mixed and used.

In one embodiment of the present invention, the molecular weight of the poly(lactide-co-glycolide) may be preferably 1 to 1,000 kDa, and more preferably 75 to 400 kDa.

In one embodiment of the present invention, the poly (lactide-co-glycolide) may have an ester or an acid, and more preferably an ester as an end group.

In one embodiment of the present invention, the organic solvent in step (i) may be selected from dichloromethane, ethyl acetate, dimethyl sulfoxide, dimethylformamide, acetic acid, hydrochloric acid, methanol, ethanol, acetone, chloroform, N-methyl-2-pyrrolidone, tetrahydrofuran, methyl ethyl ketone, propyl acetate, methyl acetate and a mixture thereof, and more preferably selected from dichloromethane, ethyl acetate and a mixture thereof.

In one embodiment of the present invention, a weight ratio of solid (the Compound of Formula 1, or a pharmaceutically acceptable salt thereof, and poly(lactide-co-glycolide)) to the organic solvent (the weight of the Compound of Formula 1+poly(lactide-co-glycolide)/the weight of the organic solvent) in step (i) may be preferably 0.05 to 0.4, and more preferably 0.08 to 0.2.

In one embodiment of the present invention, the continuous phase in step (ii) may be polyvinyl alcohol solution. For example, 1% polyvinyl alcohol solution or 2% polyvinyl alcohol solution may be used.

In one embodiment of the present invention, the preparation of the emulsion in step (ii) may be carried out by membrane emulsification.

In one embodiment of the present invention, the method for preparing a pharmaceutical composition for injection may further comprise a step of sterilizing the microsphere. In one embodiment of the present invention, the sterilization of the microsphere may be carried out, for example, with gamma rays of 10 kGy or more, or gamma rays of 25 kGy or more.

Advantageous Effects of Invention

In the present invention, by providing a pharmaceutical composition for injection in which the Compound of Formula 1—which is a prodrug of a caspase inhibitor—is used, the pharmaceutical composition for injection having the ability for sustained-release of drug in vivo for at least one month without initial burst release can be provided.

MODE FOR THE INVENTION

Hereinafter, the present invention will be described in more detail through preparation examples and examples. However, these examples are only illustrative, and the scope of the present invention is not limited thereto.

Preparation Example: Synthesis of (2S,3S)-2-(fluoromethyl)-3-((R)-5-isopropyl-3-(isoquinolin-1-yl)-4,5-dihydroisoxazole-5-carboxamido)-5-oxotetrahydrofuran-2-yl acetate Nivocasan ((R)—N-((2S,3 S)-2-(fluoromethyl)-2-hydroxy-5-oxotetrahydrofuran-3-yl]-5-isopropyl-3-(isoquinolin-1-yl)-4,5-dihydroisoxazole-5-carboxamide; 5.0 g, 12.0 mmol) was dissolved in dichloromethane (50 mL), and then acetyl chloride (0.94 mL, 13.2 mmol, 1.1 equiv), triethylamine (2.52 mL, 18.0 mmol, 1.5 equiv) and 4-dimethylaminopyridine (0.15 g, 1.2 mmol, 0.1 equiv) were added thereto while keeping the temperature at 5° C. or lower. The reaction mixture was stirred at 25° C. for about 2 hours, and the reaction was terminated by adding 10% aqueous sodium hydrogen carbonate solution (25 mL). After adding water (25 mL) and stirring, the organic layer was separated and distilled under reduced pressure. The obtained mixture was recrystallized in a 1:5 mixture of ethyl acetate and hexane (EtOAc:hexane=1:5) to obtain 3.0 g (yield: 54%) of the title compound.

$^1$H NMR (400 MHz, CDCl$_3$) δ 9.12 (d, 1H), 8.55 (d, 1H), 7.87 (d, 1H), 7.74-7.69 (m, 3H), 7.08 (d, 1H), 5.22 (m, 1H), 4.69 (d, 2H), 4.03 (d, 1H), 3.83 (d, 1H), 2.97 (m, 2H), 2.38 (m, 1H), 2.18 (s, 3H), 1.05 (dd, 6H)

Examples 1 to 7: Preparation of Microspheres Encapsulating Caspase Inhibitor Prodrug According to the compositions denoted in Table 1 below, microspheres encapsulated with the caspase inhibitor prodrug were prepared.

The Compound of Formula 1, which is a caspase inhibitor prodrug, and PLGA were weighed in a weight ratio as denoted in Table 1, and an organic solvent dichloromethane was added thereto and stirred to prepare the dispersed phase. The PLGAs used were three (3) types of 5050PLGA (L/G ratio 50:50, M.W. 38,000-54,000), 7525PLGA (L/G ratio 75:25, M.W. 76,000-115,000) and PLGA in which 5050PLGA and 7525PLGA were mixed in a weight ratio of 6:4.

For the continuous phase, 150 mL of 2% polyvinyl alcohol (M.W. 31,000-50,000, degree of hydrolysis 87-89%) or 5,100 mL of 1% polyvinyl alcohol (M.W. 31,000-50,000, degree of hydrolysis 87-89%) was used, and emulsions were prepared by membrane emulsification.

The prepared emulsions were stirred overnight at room temperature to remove solvent, repeatedly washed with sterile purified water, and then freeze-dried to obtain microspheres.

TABLE 1

| | Example 1 | Example 2 | Example 3 | Example 4 | Example 5 | Example 6 | Example 7 |
|---|---|---|---|---|---|---|---|
| Prodrug amount (g) | 3.4 | 3.4 | 0.5 | 0.5 | 0.167 | 0.333 | 0.5 |
| PLGA amount (g) | 17 | 17 | 0.5 | 0.5 | 0.833 | 0.667 | 0.5 |
| PLGA L/G ratio | 50:50 | 75:25 | 50:50 | 75:25 | 50:50 (60 wt %) 75:25 (40 wt %) | 50:50 (60 wt %) 75:25 (40 wt %) | 50:50 (60 wt %) 75:25 (40 wt %) |
| PLGA M.W. (kDa) | 38-54 | 76-115 | 38-54 | 76-115 | 38-54 (60 wt %) 76-115 (40 wt %) | 38-54 (60 wt %) 76-115 (40 wt %) | 38-54 (60 wt %) 76-115 (40 wt %) |
| Organic solvent amount (g) | 170 | 170 | 10.0 | 10.0 | 10.0 | 10.0 | 10.0 |
| PVA concentration (%, w/v) | 1 | 1 | 2 | 2 | 2 | 2 | 2 |
| PVA solution amount (mL) | 5100 | 5100 | 150 | 150 | 150 | 150 | 150 |

Experimental Example 1: Analysis of Microsphere Properties and Drug Encapsulation Rate The properties of the microspheres prepared in Examples 1 to 7 were characterized by the morphology and encapsulation rate of freeze-dried microspheres.

The morphology of the freeze-dried microspheres was observed by scanning electron microscopy. For the amount of drug encapsulated in the microspheres, 30 mg of microspheres was dissolved in 50 mL of acetonitrile, and the supernatant obtained by ultracentrifugation was analyzed by HPLC (high-performance liquid chromatography). The encapsulation efficiency was calculated by measuring the encapsulation rate.

Encapsulation rate=(weight of measured drug)/(weight of measured microspheres (MS))*100 (%)

Encapsulation efficiency=(weight of measured drug)/(weight of drug added initially)*100(%)

Figure 1:
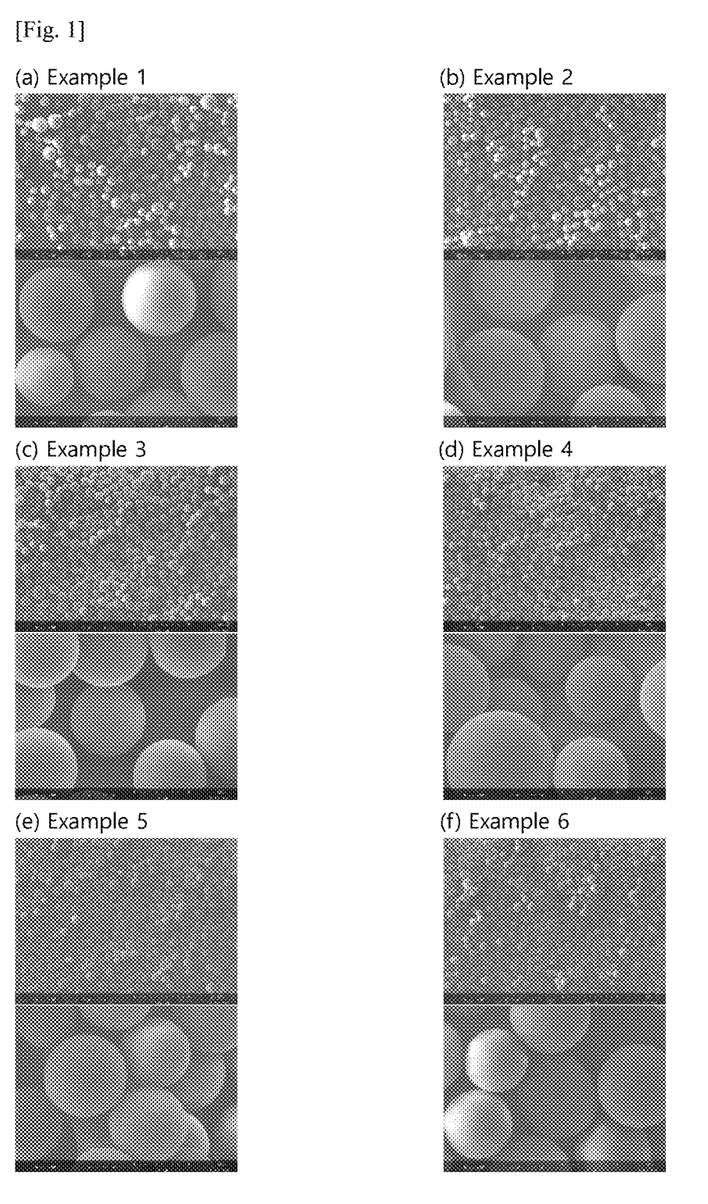
FIG. 1 is photographs taken with a scanning electron microscope (SEM) of the microspheres prepared in Examples 1 to 7.

The results observed by scanning electron microscopy are represented in FIG. 1, and the results directed to the encapsulation rate and encapsulation efficiency of the drug are summarized and represented in Table 2.

TABLE 2

| | Example 1 | Example 2 | Example 3 | Example 4 | Example 5 | Example 6 | Example 7 |
|---|---|---|---|---|---|---|---|
| Prodrug/PLGA (%, w/w) | 16.7 | 16.7 | 50 | 50 | 16.7 | 33.3 | 50 |
| Drug encapsulation rate (%, w/w) | 14.4 | 13.9 | 45.4 | 46 | 15.5 | 30.9 | 46.5 |
| Drug encapsulation efficiency (%) | 86.2 | 83.2 | 90.8 | 92 | 92.8 | 92.8 | 93 |

As can be seen from FIG. 1 and Table 2, the microspheres of the Examples encapsulating the prodrug had a uniform size and a clean surface, and showed the encapsulation efficiency of 80% or more.

Experimental Example 2: In Vitro Dissolution Test of Microspheres 1

An in vitro dissolution test of the microspheres prepared in Examples 1 to 7 was carried out. The microspheres were shaken in phosphate-buffered saline (PBS, 37° C.), the eluate was collected and filtered at specific times, and the amount of drug released was analyzed by HPLC. Because the prodrug is converted to the parent drug, caspase inhibitor, by hydrolysis in aqueous solution, the amount of the released drug was confirmed through the amount of caspase inhibitor measured by HPLC.

Figure 2:
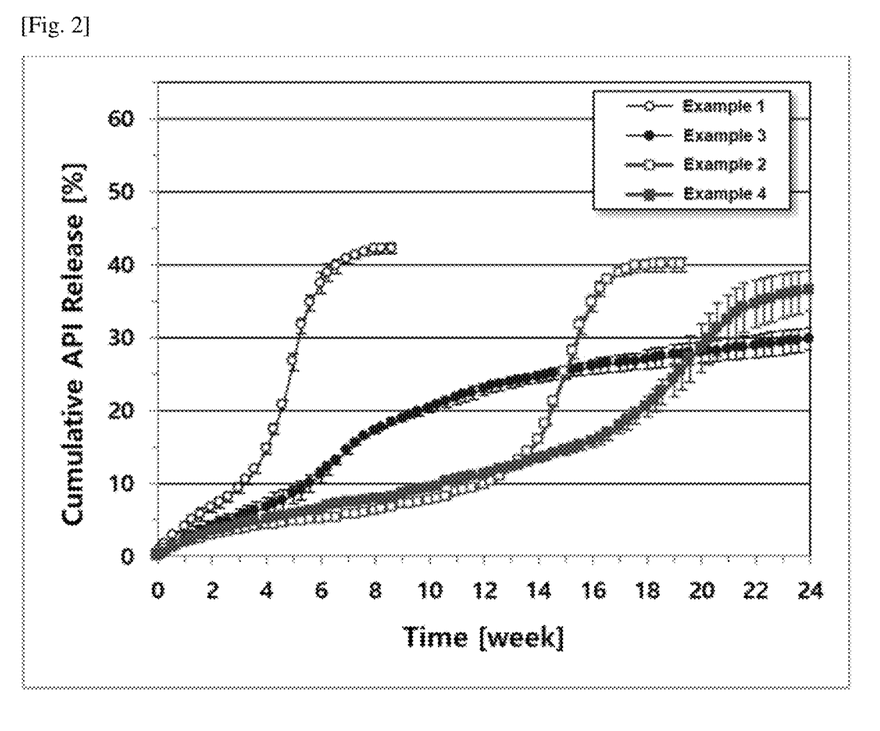
FIG. 2 is a graph showing the results of the in vitro dissolution test of the microspheres of Examples 1 to 4.
Figure 3:
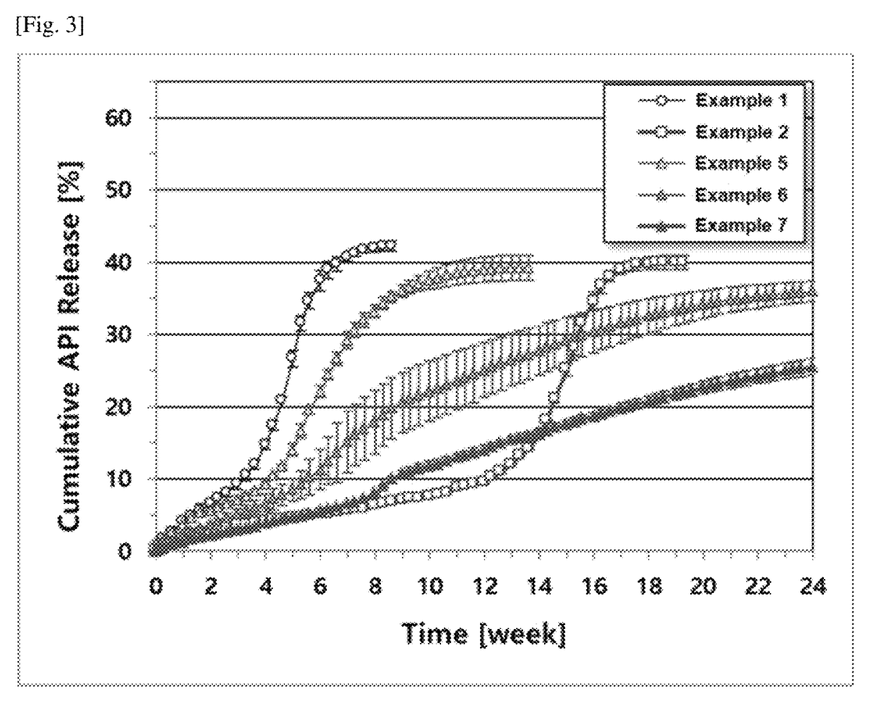
FIG. 3 is a graph showing the results of the in vitro dissolution test of the microspheres of Examples 5 to 7 in comparison with the results of the in vitro dissolution test of the microspheres of Examples 1 and 2.

The measured results of the in vitro dissolution test are represented in FIG. 2 for Examples 1 to 4, and represented in FIG. 3 for Examples 5 to 7 in comparison with Examples 1 and 2.

The drug release from the microspheres prepared in Example 1 was sustained for about 8 weeks, and the drug release from the microspheres prepared in Example 2 was sustained for about 18 weeks. This is because the hydrolysis rate is slightly slower as the L/G ratio of PLGA is changed from 50:50 to 75:25. The microspheres prepared in Examples 3 and 4 are those having a drug encapsulation rate about 3 times higher than that of the microspheres prepared in Examples 1 and 2, respectively. It was confirmed that when the drug encapsulation rate is high, the drug release is maintained a little longer. This is because it takes longer time for a larger amount of drugs to be dissolved in a constant eluate.

The PLGA used in Example 5 was designed to show intermediate characteristics between the two microspheres of Examples 1 and 2 by using the PLGA which is a mixture of the PLGA used in Examples 1 and 2. Practically, in the dissolution graph, the dissolution pattern of the microspheres prepared in Example 5 was located between the dissolution patterns of the microspheres prepared in Examples 1 and 2. The microspheres prepared in Examples 6 and 7 are those having a higher drug encapsulation rate than the microspheres prepared in Example 5, respectively.

It was confirmed that the higher the drug encapsulation rate, the longer the drug release maintained.

From the above results, it was confirmed that the dissolution pattern is changed by adjusting the type of PLGA and the content of the drug.

Figure 4:
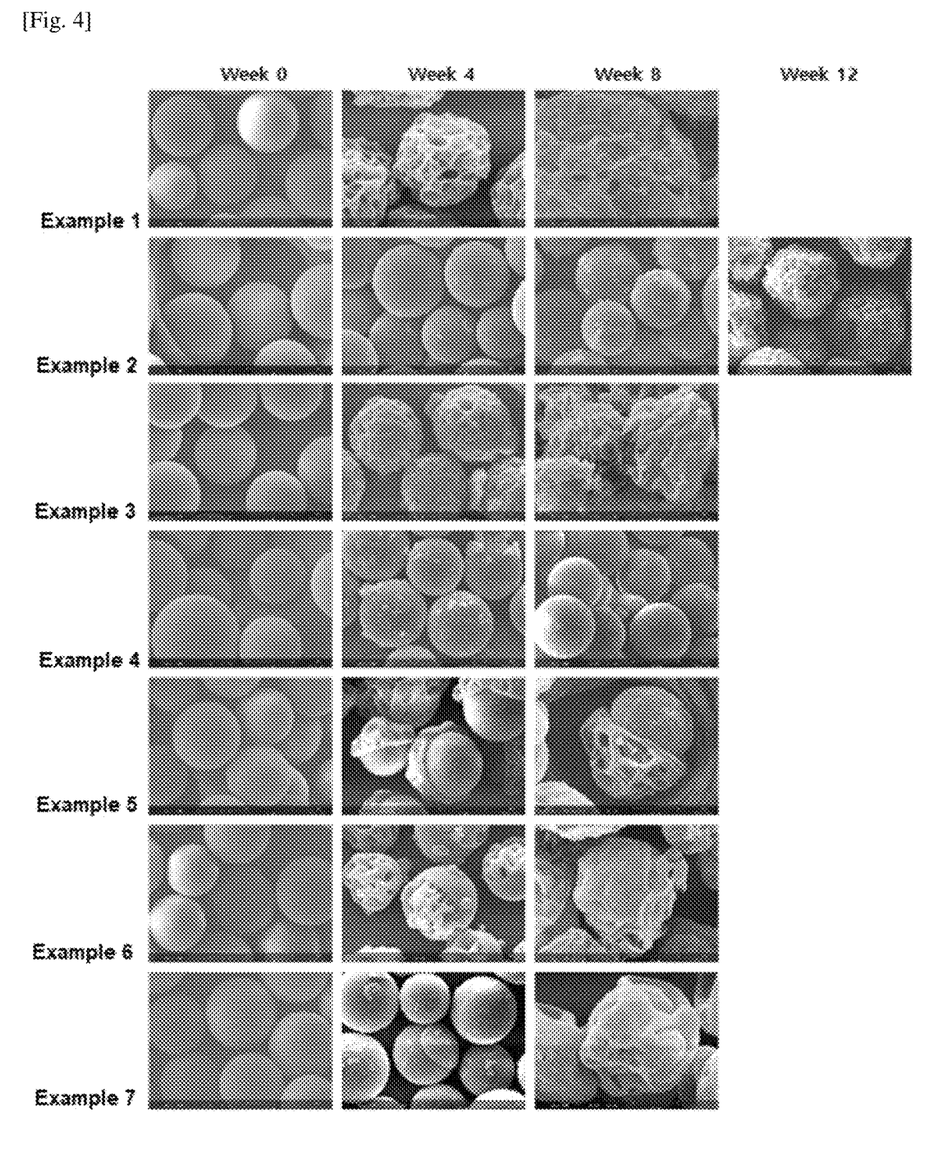
FIG. 4 is photographs taken with a scanning electron microscope of the morphologies of the microspheres of Examples 1 to 7, which changes as hydrolysis proceeds.

Experimental Example 3: Observation of Changes in Morphologies of Microspheres According to Hydrolysis The morphologies of the microspheres, which change with the progress of hydrolysis, were observed by scanning electron microscopy, and the results are represented in FIG. 4. In addition, the change in the molecular weight of PLGA in the microspheres prepared in Example 1 with the progress of hydrolysis was measured by GPC and represented in FIG. 5 as a graph of molecular weight vs. hydrolysis time.

In Examples 1 to 4, it was confirmed that when the L/G ratio of PLGA was 50:50, many pores were generated from week 4, and at week 8 the particles became larger and the pores were also enlarged due to swelling. When the L/G ratio of PLGA was 75:25, there was little change until week 8, and pore formation was observed at week 12. It can be inferred that the part where the release rate of the caspase inhibitor dramatically increases is the part where pore formation starts in the PLGA microspheres.

In the case of Examples 5 to 7 in which the mixed PLGAs were used, at week 4 of the dissolution test the microspheres were divided into two parts. One part maintained its shape well, but the other part had swelling or pores. Microspheres having a high drug encapsulation rate showed a little change of clearly dividing into two parts. At week 8, the microspheres were swollen as a whole and became larger. This division into two parts suggested that if PLGA with L/G ratio of 50:50 and PLGA with L/G ratio of 75:25 were mixed, the PLGA might not be uniformly mixed. It was observed that more hydrophilic PLGA with L/G ratio of 50:50 swelled quickly, while relatively weak hydrophilic PLGA with L/G ratio of 75:25 swelled slowly, thereby resulting in the separation of microspheres.

Figure 5:
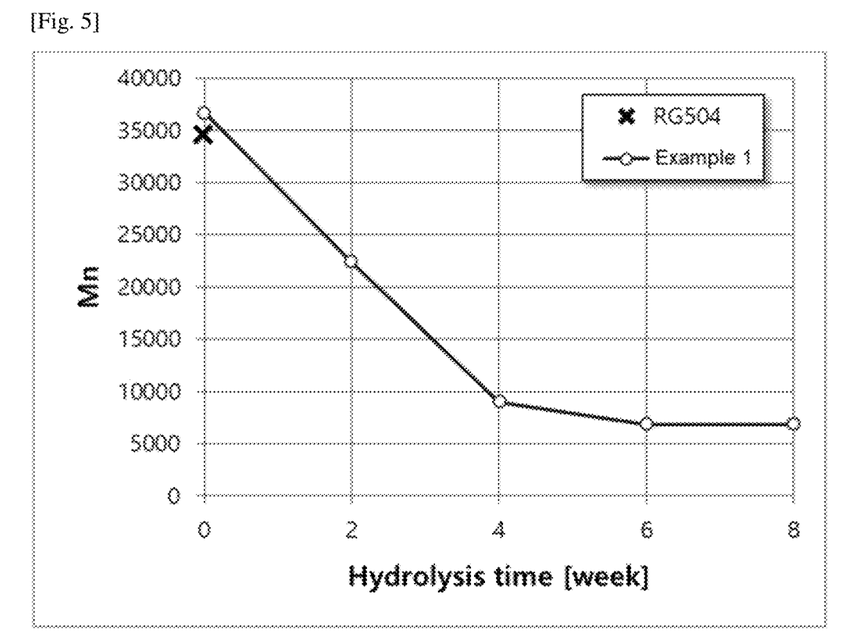
FIG. 5 is a graph showing the results of the change in PLGA molecular weight measured by GPC as the hydrolysis of the microspheres of Example 1 proceeds.

FIG. 5 is a result of measuring the change in the molecular weight of PLGA in the microspheres prepared in Example 1 by GPC according to the progress of hydrolysis. The molecular weight rapidly decreased by week 4, which was reduced to about ¼ compared to the initial stage, and thereafter the decrease amount was small.

From the above results, it can be inferred that the molecular weight decreased rapidly as hydrolysis proceeded and the release of the drug was accelerated when pores were formed.

Examples 8 to 15: Preparation of Microspheres Encapsulating Caspase Inhibitor Prodrug According to the compositions denoted in Table 3 below, microspheres encapsulated with the caspase inhibitor prodrug were prepared.

The Compound of Formula 1, which is a caspase inhibitor prodrug, and PLGA were weighed in a weight ratio as denoted in Table 3, and an organic solvent dichloromethane was added thereto and stirred to prepare the dispersed phase. The L/G ratio of PLGA used was 50:50 (M.W. 38,000-54,000).

For the continuous phase, 4,800 mL of 1% polyvinyl alcohol (M.W. 31,000-50,000, degree of hydrolysis 87-89%) was used, and emulsions were prepared by membrane emulsification.

The prepared emulsions were stirred overnight at room temperature to remove solvent, repeatedly washed with sterile purified water, and then freeze-dried to obtain microspheres.

Each sample was sterilized by varying the intensity of gamma rays from 0 to 25 kGy.

TABLE 3

| | Example 8 | Example 9 | Example 10 | Example 11 | Example 12 | Example 13 | Example 14 | Example 15 |
|---|---|---|---|---|---|---|---|---|
| Prodrug amount (g) | 6 | 6 | 6 | 6 | 10 | 10 | 10 | 10 |
| PLGA amount (g) | 14 | 14 | 14 | 14 | 10 | 10 | 10 | 10 |
| PLGA L/G ratio | 50:50 | 50:50 | 50:50 | 50:50 | 50:50 | 50:50 | 50:50 | 50:50 |
| PLGA M.W. (kDa) | 38-54 | 38-54 | 38-54 | 38-54 | 38-54 | 38-54 | 38-54 | 38-54 |
| Organic solvent amount (g) | 200 | 200 | 200 | 200 | 200 | 200 | 200 | 200 |
| PVA concentration (%, w/v) | 1 | 1 | 1 | 1 | 1 | 1 | 1 | 1 |
| PVA solution amount (mL) | 4,800 | 4,800 | 4,800 | 4,800 | 4,800 | 4,800 | 4,800 | 4,800 |
| Gamma ray sterilization intensity (kGy) | 0 | 15 | 20 | 25 | 0 | 15 | 20 | 25 |

Comparative Examples 1 to 6: Preparation of Microspheres not Encapsulating Caspase Inhibitor Prodrug According to the compositions denoted in Table 4 below, microspheres not encapsulated with the caspase inhibitor prodrug were prepared.

An organic solvent dichloromethane was added to PLGA and stirred to prepare the dispersed phase. The L/G ratio of PLGA used was 50:50 (M.W. 38,000-54,000).

For the continuous phase, 4,800 mL of 1% polyvinyl alcohol (M.W. 31,000-50,000, degree of hydrolysis 87-89%) was used, and emulsions were prepared by membrane emulsification.

The prepared emulsions were stirred overnight at room temperature to remove solvent, repeatedly washed with sterile purified water, and then freeze-dried to obtain microspheres.

Each sample was sterilized by varying the intensity of gamma rays from 0 to 25 kGy.

TABLE 4

|  | Comparative Example | | | | | |
| --- | --- | --- | --- | --- | --- | --- |
|  | Comparative Example 1 | Comparative Example 2 | Comparative Example 3 | Comparative Example 4 | Comparative Example 5 | Comparative Example 6 |
| PLGA amount (g) | 20 | 20 | 20 | 20 | 20 | 20 |
| PLGA L/G ratio | 50:50 | 50:50 | 50:50 | 50:50 | 50:50 | 50:50 |
| PLGA M.W. (kDa) | 38-54 | 38-54 | 38-54 | 38-54 | 38-54 | 38-54 |
| Organic solvent amount (g) | 200 | 200 | 200 | 200 | 200 | 200 |
| PVA concentration (%, w/v) | 1 | 1 | 1 | 1 | 1 | 1 |
| PVA solution amount (mL) | 4,800 | 4,800 | 4,800 | 4,800 | 4,800 | 4,800 |
| Gamma ray sterilization intensity (kGy) | 0 | 5 | 10 | 15 | 20 | 25 |

Experimental Example 4: In Vitro Dissolution Test of Microspheres 2

An in vitro dissolution test of the microspheres prepared in Examples 8 to 15 was carried out. The microspheres were shaken in phosphate-buffered saline (PBS, 37° C.), the eluate was collected and filtered at specific times, and the amount of drug released was analyzed by HPLC. Because the prodrug is converted to the parent drug, caspase inhibitor, by hydrolysis in aqueous solution, the amount of the released drug was confirmed through the amount of caspase inhibitor measured by HPLC.

Figure 6:
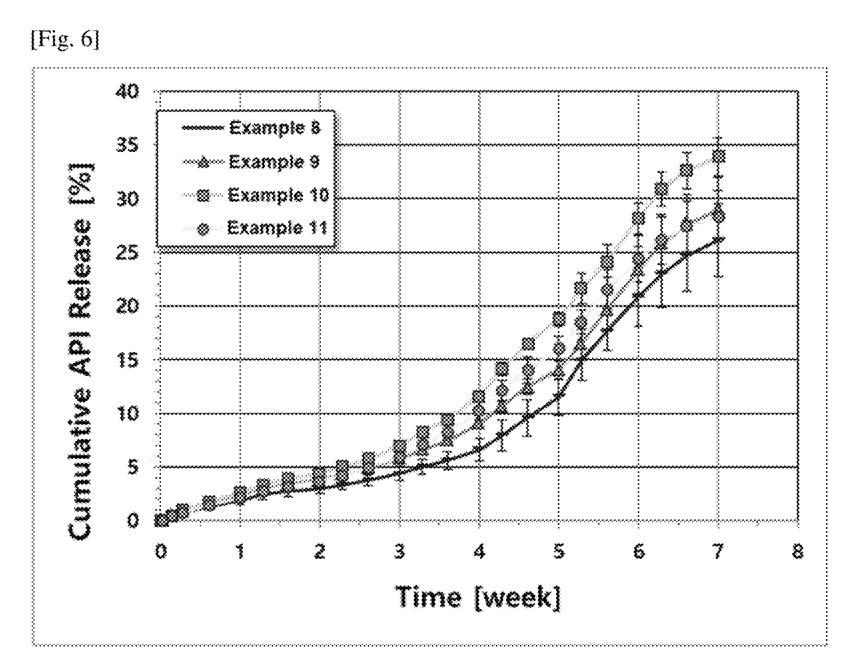
FIG. 6 is a graph showing the results of the in vitro dissolution test of the microspheres of Examples 8 to 11.
Figure 7:
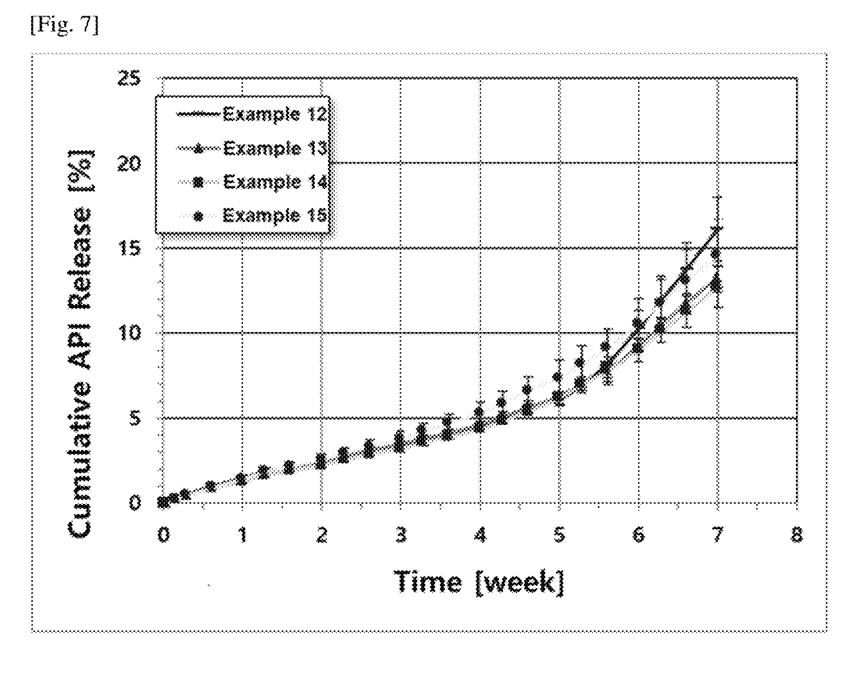
FIG. 7 is a graph showing the results of the in vitro dissolution test of the microspheres of Examples 12 to 15.

The measured results of the in vitro dissolution test are represented in FIG. 6 for Examples 8 to 11, and represented in FIG. 7 for Examples 12 to 15.

From FIG. 6, it was confirmed that the microspheres prepared in Examples 8 to 11 showed a similar elution pattern, but gamma rays affect the dissolution. Although the relationship of the increase in the amount of dissolution with the increase of the intensity of gamma rays was not clear, there was a tendency that the microspheres irradiated with gamma rays showed to proceed with dissolution a little faster. RG504 in FIG. 6 represents the molecular weight of PLGA before preparing the microspheres.

FIG. 7 is a graph showing the dissolution pattern of the microspheres prepared in Examples 12 to 15, and all of which showed a similar dissolution pattern. It was not easy to understand the effect of the intensity of gamma rays on the dissolution pattern. It was thought that this may be because the microspheres prepared in Examples 12 to 15 had a larger amount of the encapsulated drug than the microspheres prepared in Examples 8 to 11 and the content of PLGA was reduced, so that the effect of PLGA on dissolution may be reduced.

Experimental Example 5: Observation of Changes in Properties of Microspheres According to Gamma Ray Intensity The change in the molecular weight of PLGA according to the intensity of gamma rays was measured by GPC (gel permeation chromatography), and the results are represented in FIG. 8.

Figure 8:
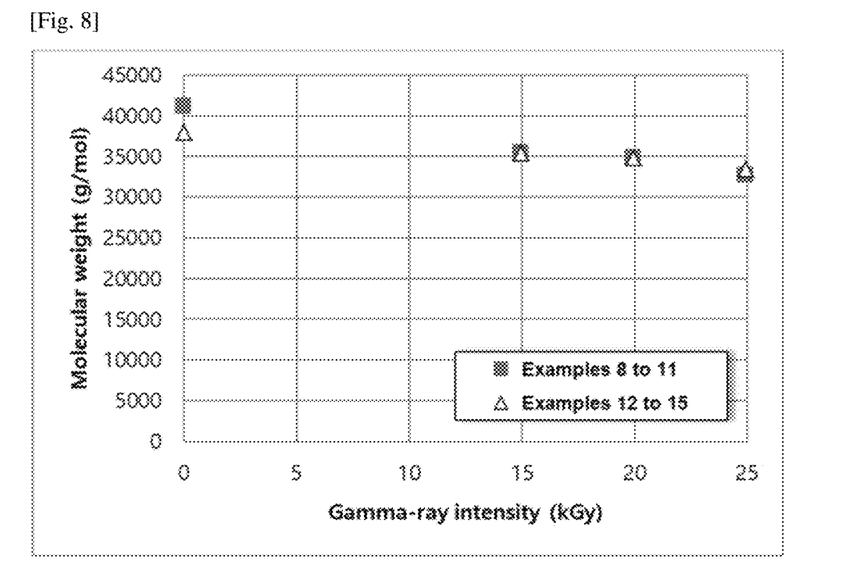
FIG. 8 is a graph showing the change in PLGA molecular weight of the microspheres of Examples 11 to 15 according to the intensity of gamma rays.

As can be seen from FIG. 8, as the intensity of gamma rays increased, the molecular weight decreased more. When gamma rays were irradiated with the intensity of 25 kGy, it was confirmed that the molecular weight of PLGA having L/G ratio of 50:50 decreased by about 20%.

Experimental Example 6: Sterility Test (the Korean Pharmacopoeia: Sterility Test/ISO 11737-2)

The sterility was measured in the microspheres prepared in Comparative Examples 1 to 6 by the use of a microorganism test method, and the results are represented in Table 5.

TABLE 5

| Media | Sample | Result | Media | Sample | Result |
| --- | --- | --- | --- | --- | --- |
| Fluid Thioglycollate Medium I (Aerobic bacteria) | Control | Negative (−) | Tryptic Soy Broth (Fungus) | Control | Negative (−) |
|  | Comparative Example 1 | Positive (+) |  | Comparative Example 1 | Positive (+) |
|  | Comparative Example 2 | Positive (+) |  | Comparative Example 2 | Negative (−) |
|  | Comparative Example 3 | Negative (−) |  | Comparative Example 3 | Negative (−) |
|  | Comparative Example 4 | Negative (−) |  | Comparative Example 4 | Negative (−) |
|  | Comparative Example 5 | Negative (−) |  | Comparative Example 5 | Negative (−) |
|  | Comparative Example 6 | Negative (−) |  | Comparative Example 6 | Negative (−) |

Sterility was tested by the presence or absence of aerobic bacteria and fungi. It was confirmed that aerobic bacteria were eliminated at gamma rays of 10 kGy or higher, and fungi were eliminated at gamma rays of 5 kGy or higher. Therefore, it can be known that the sterile state was achieved at 10 kGy or more, and the sufficient sterile state was obtained at 25 kGy.

Examples 16 to 33: Preparation of Microspheres Encapsulating Caspase Inhibitor Prodrug According to the compositions denoted in Tables 6 and 7 below, microspheres encapsulated with the caspase inhibitor prodrug were prepared.

The Compound of Formula 1, which is a caspase inhibitor prodrug, and PLGA were weighed in a weight ratio as denoted in Tables 6 and 7, and an organic solvent dichloromethane was added with the weight ratio of the solid (Compound of Formula 1+PLGA) to the organic solvent dichloromethane of 1:10 or 1:3.3 as denoted in Tables 6 and 7, and stirred to prepare the dispersed phase. The PLGA used was a polymer obtained by mixing the first polymer and the second polymer in a weight ratio of 60:40. As the first polymer, 5050PLGA (L/G ratio 50:50, M.W. 38,000-54,000) was used, and as the second polymer, one of the following three (3) polymers a, b and c was selected.

a. L/G ratio 75:25, M.W. 76,000-115,000, Ester terminated
b. L/G ratio 75:25, M.W. 30,000-34,000, Ester terminated
c. L/G ratio 75:25, M.W. 4,000-15,000, Acid terminated For the continuous phase, 150 mL of 2% polyvinyl alcohol (M.W. 31,000-50,000, degree of hydrolysis 87-89%) was used, and emulsions were prepared by membrane emulsification.

The prepared emulsions were stirred overnight at room temperature to remove solvent, repeatedly washed with sterile purified water, and then freeze-dried to obtain microspheres.

TABLE 6

| | Example 16 | Example 17 | Example 18 | Example 19 | Example 20 | Example 21 | Example 22 | Example 23 | Example 24 |
|---|---|---|---|---|---|---|---|---|---|
| Prodrug amount (g) | 0.333 | 0.556 | 0.556 | 0.9 | 0.9 | 0.333 | 0.333 | 0.556 | 0.556 |
| PLGA amount (g) | 1.667 | 1.444 | 1.444 | 1.1 | 1.1 | 1.667 | 1.667 | 1.444 | 1.444 |
| PLGA L/G Ratio | 50:50 (60 wt %) 75:25 (40 wt %) | 50:50 (60 wt %) 75:25 (40 wt %) | 50:50 (60 wt %) 75:25 (40 wt %) | 50:50 (60 wt %) 75:25 (40 wt %) | 50:50 (60 wt %) 75:25 (40 wt %) | 50:50 (60 wt %) 75:25 (40 wt %) | 50:50 (60 wt %) 75:25 (40 wt %) | 50:50 (60 wt %) 75:25 (40 wt %) | 50:50 (60 wt %) 75:25 (40 wt %) |
| PLGA M.W. (kDa) | 38-54 (60 wt %) 30-34 (40 wt %) | 38-54 (60 wt %) 30-34 (40 wt %) | 38-54 (60 wt %) 76-115 (40 wt %) | 38-54 (60 wt %) 30-34 (40 wt %) | 38-54 (60 wt %) 76-115 (40 wt %) | 38-54 (60 wt %) 30-34 (40 wt %) | 38-54 (60 wt %) 76-115 (40 wt %) | 38-54 (60 wt %) 30-34 (40 wt %) | 38-54 (60 wt %) 76-115 (40 wt %) |
| PLGA End Group | Ester | Ester | Ester | Ester | Ester | Ester | Ester | Ester | Ester |
| Organic solvent amount (g) | 20 | 20 | 20 | 20 | 20 | 10 | 10 | 10 | 10 |
| PVA concentration (%, w/v) | 2 | 2 | 2 | 2 | 2 | 2 | 2 | 2 | 2 |
| PVA solution amount (mL) | 150 | 150 | 150 | 150 | 150 | 150 | 150 | 150 | 150 |

TABLE 7

| | Example 25 | Example 26 | Example 27 | Example 28 | Example 29 | Example 30 | Example 31 | Example 32 | Example 33 |
|---|---|---|---|---|---|---|---|---|---|
| Prodrug amount (g) | 0.9 | 0.9 | 0.333 | 0.9 | 0.556 | 0.333 | 0.556 | 0.9 | 0.556 |
| PLGA amount (g) | 1.1 | 1.1 | 1.667 | 1.1 | 1.444 | 1.667 | 1.444 | 1.1 | 1.444 |
| PLGA L/G Ratio | 50:50 (60 wt %) 75:25 (40 wt %) | 50:50 (60 wt %) 75:25 (40 wt %) | 50:50 (60 wt %) 75:25 (40 wt %) | 50:50 (60 wt %) 75:25 (40 wt %) | 50:50 (60 wt %) 75:25 (40 wt %) | 50:50 (60 wt %) 75:25 (40 wt %) | 50:50 (60 wt %) 75:25 (40 wt %) | 50:50 (60 wt %) 75:25 (40 wt %) | 50:50 (60 wt %) 75:25 (40 wt %) |
| PLGA M.W. (kDa) | 38-54 (60 wt %) 30-34 (40 wt %) | 38-54 (60 wt %) 76-115 (40 wt %) | 38-54 (60 wt %) 76-115 (40 wt %) | 38-54 (60 wt %) 30-34 (40 wt %) | 38-54 (60 wt %) 4-15 (40 wt %) | 38-54 (60 wt %) 4-15 (40 wt %) | 38-54 (60 wt %) 4-15 (40 wt %) | 38-54 (60 wt %) 4-15 (40 wt %) | 38-54 (60 wt %) 4-15 (40 wt %) |
| PLGA End Group | Ester | Ester | Ester | Ester | Acid | Acid | Acid | Acid | Acid |
| Organic solvent amount (g) | 10 | 10 | 6.7 | 6.7 | 20 | 10 | 10 | 10 | 6.7 |
| PVA concentration (%, w/v) | 2 | 2 | 2 | 2 | 2 | 2 | 2 | 2 | 2 |
| PVA solution amount (mL) | 150 | 150 | 150 | 150 | 150 | 150 | 150 | 150 | 150 |

Experimental Example 7: Pharmacokinetics (PK) Test 1

The PK test was carried out in dogs using microspheres prepared in Examples 3 to 5 and 16 to 33. The microspheres prepared in Examples 3 and 4 at a concentration of 30 mg/ml, and the microspheres prepared in Examples 5 and 16 to 33 at a concentration of 50 mg/ml were administered to the joint cavity, and joint synovial fluid was collected at a specific time point to measure the concentration of caspase inhibitor.

Figure 9:
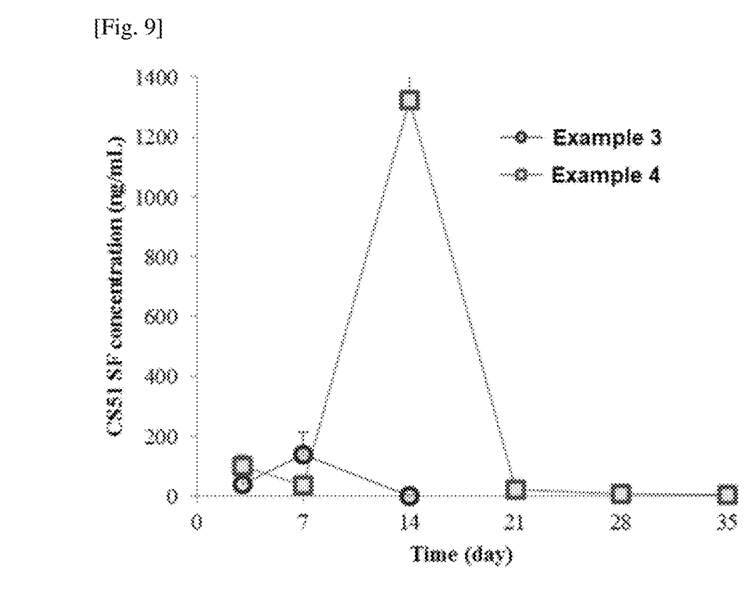
FIG. 9 is a graph showing the PK test results of the microspheres of Examples 3 and 4.
Figure 10:
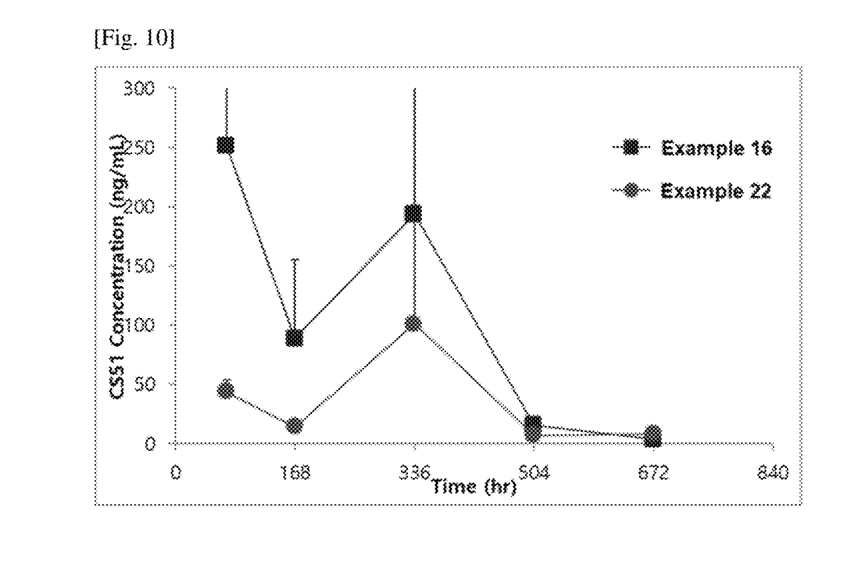
FIG. 10 is a graph showing the PK test results of the microspheres of Examples 16 and 22.

The PK test results of the microspheres prepared in Examples 3 and 4 are represented in FIG. 9. Among the microspheres prepared in Examples 5 and 16 to 33, the microspheres prepared in Examples 16 and 22—in which the concentration of the caspase inhibitor was maintained at a constant level for up to 2 weeks, thereby showing sustained release of 2 weeks or more—were measured up to 4 weeks, and the results are represented in FIG. 10.

From the PK test result, when other conditions were the same, the initial release amount decreased as the encapsulation rate of the prodrug was lower. When other conditions were the same, the polymer with a higher molecular weight decreased the initial release amount. When other conditions were the same, the initial release amount slightly increased when the ratio of solid to organic solvent was high.

Examples 34 to 40: Preparation of Microspheres Encapsulating Caspase Inhibitor Prodrug According to the compositions denoted in Table 8 below, microspheres encapsulated with the caspase inhibitor prodrug were prepared.

The Compound of Formula 1, which is a caspase inhibitor prodrug, and PLGA were weighed in a weight ratio as denoted in Table 8, and an organic solvent dichloromethane was added with the weight ratio of the solid (Compound of Formula 1+PLGA) to the organic solvent dichloromethane of 1:10 or 1:5 as denoted in Table 8, and stirred to prepare the dispersed phase. As a single polymer, 7525PLGA (L/G ratio 75:25, MW 76,000-115,000) or 8515PLGA (L/G ratio 85:15, MW 190,000-240,000) was used, and as a mixed polymer, a polymer in which the first polymer and the second polymer were mixed in a weight ratio of 6:4 to 2:8 was used. For the mixed polymer, one of the following three (3) combinations a, b and c was selected.

a. The first polymer: 5050PLGA (L/G ratio 50:50, M.W. 38,000-54,000), the second polymer: 7525PLGA (L/G ratio 75:25, M.W. 76,000-115,000), the weight ratio of the first polymer and the second polymer is 6:4
b. The first polymer: 5050PLGA (L/G ratio 50:50, M.W. 38,000-54,000), the second polymer: 7525PLGA (L/G ratio 75:25, M.W. 76,000-115,000), the weight ratio of the first polymer and the second polymer is 2:8
c. The first polymer: 7525PLGA (L/G ratio 75:25, M.W. 76,000-115,000), the second polymer: 8515PLGA (L/G ratio 85:15, M.W. 190,000-240,000), the weight ratio of the first polymer and the second polymer is 5:5

For the continuous phase, 150 mL of 2% polyvinyl alcohol (M.W. 31,000-50,000, degree of hydrolysis 87-89%) was used, and emulsions were prepared by membrane emulsification.

The prepared emulsions were stirred overnight at room temperature to remove solvent, repeatedly washed with sterile purified water, and then freeze-dried to obtain microspheres.

TABLE 8

| | Example | | | | | | |
|---|---|---|---|---|---|---|---|
| | Example 34 | Example 35 | Example 36 | Example 37 | Example 38 | Example 39 | Example 40 |
| Prodrug amount (g) | 0.222 | 0.333 | 0.333 | 0.333 | 0.333 | 0.333 | 0.333 |
| PLGA amount (g) | 1.778 | 1.667 | 1.667 | 1.667 | 1.667 | 1.667 | 1.667 |
| PLGA L/G Ratio | 50:50 (60 wt %) 75:25 (40 wt %) | 50:50 (20 wt %) 75:25 (80 wt %) | 75:25 (50 wt %) 85:15 (50 wt %) | 75:25 | 75:25 | 85:15 | 85:15 |
| PLGA M.W. (kDa) | 38-54 (60 wt %) 76-115 (40 wt %) | 38-54 (60 wt %) 76-115 (40 wt %) | 76-115 (50 wt %) 190-240 (50 wt %) | 76-115 | 76-115 | 190-240 | 190-240 |
| PLGA End Group | Ester | Ester | Ester | Ester | Ester | Ester | Ester |
| Organic solvent amount (g) | 10.0 | 20.0 | 20.0 | 20.0 | 10.0 | 20.0 | 10.0 |
| PVA concentration (%, w/v) | 2 | 2 | 2 | 2 | 2 | 2 | 2 |
| PVA solution amount (mL) | 150 | 150 | 150 | 150 | 150 | 150 | 150 |

Experimental Example 8: Pharmacokinetic (PK) Test 2

Figure 11:
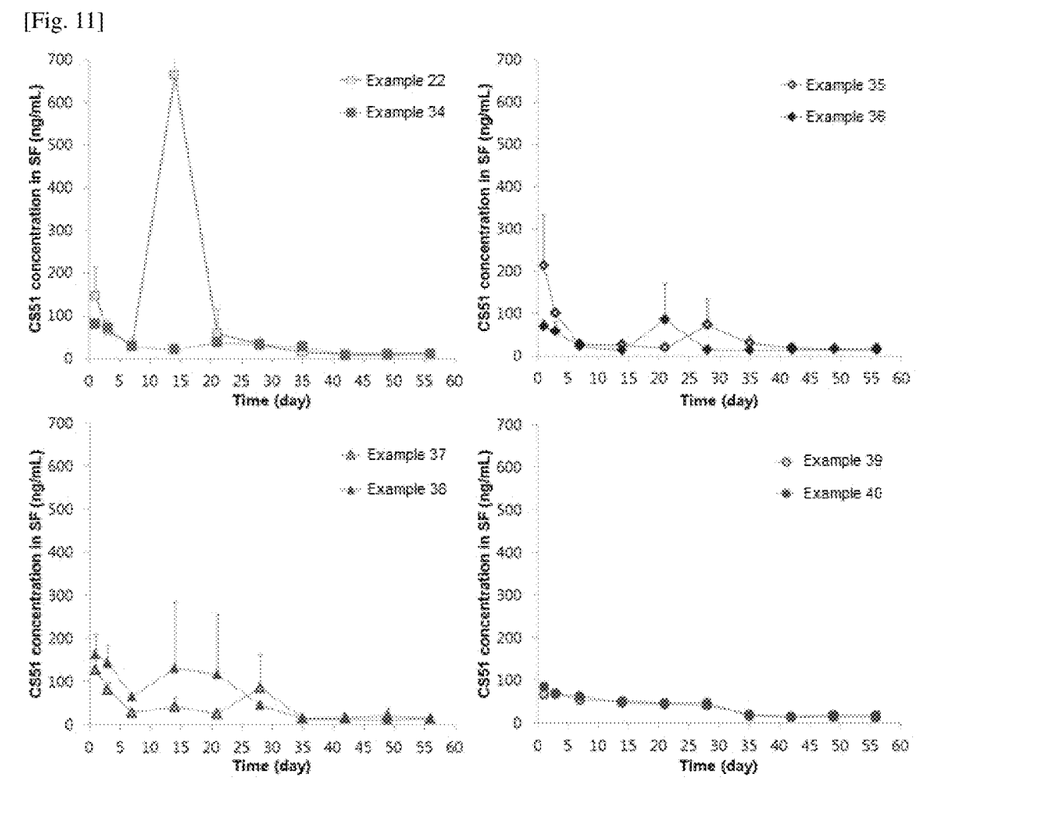
FIG. 11 is a graph showing the PK test results of the microspheres of Examples 22 and 34 to 40.
Figure 12:
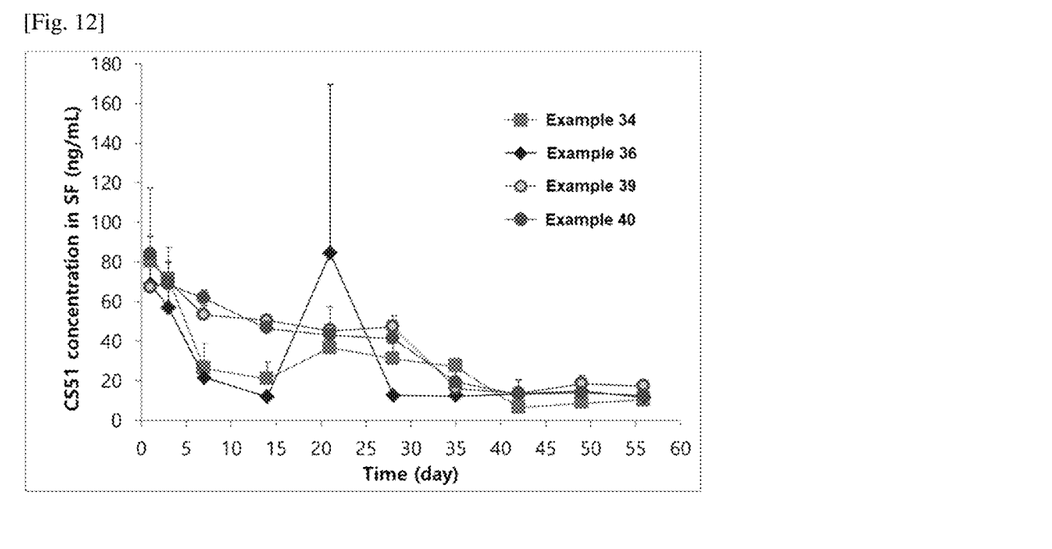
FIG. 12 is a graph showing the PK test results of the microspheres prepared in Examples 34, 36, 39 and 40 on a smaller scale.

The PK test was carried out in dogs using microspheres prepared in Examples 22 and 34 to 40. Microspheres at a concentration of 50 mg/ml were administered to the joint cavity, and joint synovial fluid was collected at a specific time point to measure the concentration of caspase inhibitor, and the results are represented in FIG. 11. The PK test results of the microspheres prepared in Examples 34, 36, 39 and 40 compared on a smaller scale are represented in FIG. 12.

In all microspheres, no initial burst was observed. In the microspheres prepared in Example 22, the concentration of the caspase inhibitor increased significantly at week 2, and the concentration continued thereafter. Contrary to this, in the microspheres prepared in Examples 34 to 40, the caspase inhibitor was continuously released without burst release for 8 weeks.

The invention claimed is:

1. A pharmaceutical composition for injection comprising a microsphere which comprises (2S,3S)-2-(fluoromethyl)-3-((R)-5-isopropyl-3-(isoquinolin-1-yl)-4,5-dihydroisoxazole-5-carboxamido)-5-oxotetrahydrofuran-2-yl acetate, or a pharmaceutically acceptable salt or isomer thereof as an active ingredient; and poly(lactide-co-glycolide) as a biocompatible polymer.

2. The pharmaceutical composition for injection according to claim 1, wherein a weight ratio of (2S,3S)-2-(fluoromethyl)-3-((R)-5-isopropyl-3-(isoquinolin-1-yl)-4,5-dihydroisoxazole-5-carboxamido)-5-oxotetrahydrofuran-2-yl acetate, or a pharmaceutically acceptable salt or isomer thereof to poly(lactide-co-glycolide) is 0.01 to 0.7.

3. The pharmaceutical composition for injection according to claim 2, wherein the weight ratio of (2S,3S)-2-(fluoromethyl)-3-((R)-5-isopropyl-3-(isoquinolin-1-yl)-4,5-dihydroisoxazole-5-carboxamido)-5-oxotetrahydrofuran-2-yl acetate, or a pharmaceutically acceptable salt or isomer thereof to poly(lactide-co-glycolide) is 0.1 to 0.4.

4. The pharmaceutical composition for injection according to claim 1, wherein a molar ratio of lactide to glycolide of the poly(lactide-co-glycolide) is 40:60 to 90:10.

5. The pharmaceutical composition for injection according to claim 4, wherein the molar ratio of lactide to glycolide of the poly(lactide-co-glycolide) is 70:30 to 90:10.

6. The pharmaceutical composition for injection according to claim 1, wherein a molecular weight of the poly(lactide-co-glycolide) is 1 to 1,000 kDa.

7. The pharmaceutical composition for injection according to claim 6, wherein the molecular weight of the poly(lactide-co-glycolide) is 75 to 400 kDa.

8. The pharmaceutical composition for injection according to claim 1, wherein an end group of the poly(lactide-co-glycolide) is ester or acid.

9. The pharmaceutical composition for injection according to claim 8, wherein the end group of the poly(lactide-co-glycolide) is ester.

10. The pharmaceutical composition for injection according to claim 1, which further comprises a solvent.

11. The pharmaceutical composition for injection according to claim 10, wherein the solvent is water, saline or phosphate-buffered saline.

12. A method for prevention or treatment of a disease in a subject, comprising administering to the subject in need thereof an effective amount of the pharmaceutical composition for injection according to claim 1, wherein the disease is selected from apoptosis-associated diseases, inflammatory diseases, osteoarthritis, rheumatoid arthritis, degenerative arthritis and destructive bone disorders.

13. A method for prevention, treatment or pain relief of osteoarthritis in a subject, comprising administering to the subject in need thereof an effective amount of the pharmaceutical composition for injection according to claim 1.

14. A method for preparing a pharmaceutical composition for injection comprising:
i) preparing a dispersed phase by dissolving (2S,3S)-2-(fluoromethyl)-3-((R)-5-isopropyl-3-(isoquinolin-1-yl)-4,5-dihydroisoxazole-5-carboxamido)-5-oxotetrahydrofuran-2-yl acetate, or a pharmaceutically acceptable salt or isomer thereof as an active ingredient; and poly(lactide-co-glycolide) as a biocompatible polymer in an organic solvent;
ii) preparing an emulsion by adding the dispersed phase obtained in step (i) to a continuous phase; and
iii) removing a solvent from the emulsion obtained in step (ii) and freeze-drying to obtain a microsphere.

15. The method for preparing a pharmaceutical composition for injection according to claim 14, wherein a weight ratio of (2S,3S)-2-(fluoromethyl)-3-((R)-5-isopropyl-3-(isoquinolin-1-yl)-4,5-dihydroisoxazole-5-carboxamido)-5-oxotetrahydrofuran-2-yl acetate, or a pharmaceutically acceptable salt or isomer thereof to poly(lactide-co-glycolide) in step (i) is 0.01 to 0.7.

16. The method for preparing a pharmaceutical composition for injection according to claim 14, wherein a weight ratio of (2S,3S)-2-(fluoromethyl)-3-((R)-5-isopropyl-3-(isoquinolin-1-yl)-4,5-dihydroisoxazole-5-carboxamido)-5-oxotetrahydrofuran-2-yl acetate, or a pharmaceutically acceptable salt or isomer thereof to poly(lactide-co-glycolide) in step (i) is 0.1 to 0.4.

17. The method for preparing a pharmaceutical composition for injection according to claim 14, wherein a molar ratio of lactide to glycolide of the poly(lactide-co-glycolide) is 40:60 to 90:10.

18. The method for preparing a pharmaceutical composition for injection according to claim 17, wherein the molar ratio of lactide to glycolide of the poly(lactide-co-glycolide) is 70:30 to 90:10.

19. The method for preparing a pharmaceutical composition for injection according to claim 14, wherein a molecular weight of the poly(lactide-co-glycolide) is 1 to 1,000 kDa.

20. The method for preparing a pharmaceutical composition for injection according to claim 19, wherein the molecular weight of the poly(lactide-co-glycolide) is 75 to 400 kDa.

21. The method for preparing a pharmaceutical composition for injection according to claim 14, wherein an end group of the poly(lactide-co-glycolide) is ester or acid.

22. The method for preparing a pharmaceutical composition for injection according to claim 21, wherein the end group of the poly(lactide-co-glycolide) is ester.

23. The method for preparing a pharmaceutical composition for injection according to claim 14, wherein the organic solvent of step (i) is selected from dichloromethane, ethyl acetate, dimethyl sulfoxide, dimethylformamide, acetic acid, hydrochloric acid, methanol, ethanol, acetone, chloroform, N-methyl-2-pyrrolidone, tetrahydrofuran, methyl ethyl ketone, propyl acetate, methyl acetate and a mixture thereof.

24. The method for preparing a pharmaceutical composition for injection according to claim 14, wherein a weight ratio of solid ((2S,3S)-2-(fluoromethyl)-3-((R)-5-isopropyl-3-(isoquinolin-1-yl)-4,5-dihydroisoxazole-5-carboxamido)-5-oxotetrahydrofuran-2-yl acetate, or a pharmaceutically acceptable salt thereof, and poly(lactide-co-glycolide)) to the organic solvent in step (i) is 0.05 to 0.4.

25. The method for preparing a pharmaceutical composition for injection according to claim 24, wherein the weight ratio of solid ((2S,3S)-2-(fluoromethyl)-3-((R)-5-isopropyl-3-(isoquinolin-1-yl)-4,5-dihydroisoxazole-5-carboxamido)-5-oxotetrahydrofuran-2-yl acetate, or a pharmaceutically acceptable salt thereof, and poly(lactide-co-glycolide)) to the organic solvent in step (i) is 0.08 to 0.2.

26. The method for preparing a pharmaceutical composition for injection according to claim 14, wherein the continuous phase of step (ii) is polyvinyl alcohol solution.

27. The method for preparing a pharmaceutical composition for injection according to claim 14, wherein the preparation of the emulsion in step (ii) is carried out by membrane emulsification.

28. The method for preparing a pharmaceutical composition for injection according to claim 14, which further comprises a step of sterilizing the microsphere.

29. The method for preparing a pharmaceutical composition for injection according to claim 28, wherein the sterilization of the microsphere is carried out with gamma rays of 10 kGy or more.

30. The method for preparing a pharmaceutical composition for injection according to claim 29, wherein the sterilization of the microsphere is carried out with gamma rays of 25 kGy or more.

* * * * *